US012616513B2

(12) United States Patent  
Cancilla et al.

(10) Patent No.: US 12,616,513 B2  
(45) Date of Patent: May 5, 2026

(54) MEDICAL DEVICE

(71) Applicant: Arbutus Medical Inc., Vancouver (CA)

(72) Inventors: Michael Cancilla, Vancouver (CA); Radu Postole, Abbotsford (CA); Geoff Borgmann, Vancouver (CA); Feyi Gbadamosi, Vancouver (CA); Julia Hudea, Vancouver (CA); John Kodosky, Helotes, TX (US); Gregory Pereira, Chapel Hill, NC (US)

(73) Assignee: ARBUTUS MEDICAL INC., Vancouver (CA)

( * ) Notice: Subject to any disclaimer, the term of this patent is extended or adjusted under 35 U.S.C. 154(b) by 616 days.

(21) Appl. No.: 17/961,934

(22) Filed: Oct. 7, 2022

(65) Prior Publication Data

US 2024/0115303 A1 Apr. 11, 2024

(51) Int. Cl.
| | |
|---|---|
| *A61B 17/66* | (2006.01) |
| *A61B 17/00* | (2006.01) |
| *A61B 17/64* | (2006.01) |
| *A61B 17/88* | (2006.01) |

(52) U.S. Cl.
CPC ...... *A61B 17/8869* (2013.01); *A61B 17/8861* (2013.01)

(58) Field of Classification Search
CPC ............ A61B 17/8869; A61B 17/8861; A61B 17/6408; A61B 17/60–666; A61B 90/14; A61B 90/50; A61B 90/57; A61B 2090/031; A61B 17/66; A61B 17/6458; A61B 2017/00486; A61B 17/6441; A61F 5/042; A61F 5/048; A61F 5/3707; A61H 1/0218; A61H 1/0222; A61H 1/024; A61H 1/0244; A61H 1/0255; A61H 1/0266

USPC .......................................................... 602/37  
See application file for complete search history.

(56) References Cited

U.S. PATENT DOCUMENTS

| | | | | |
|---|---|---|---|---|
| 1,967,471 | A | * | 7/1934 | Ettinger ............. A61B 17/6408 602/37 |
| 3,088,460 | A | * | 5/1963 | Wright ............... A61B 17/6408 602/37 |
| 4,342,309 | A | * | 8/1982 | Eftekhar ............ A61B 17/1697 606/104 |
| 4,501,267 | A | * | 2/1985 | Pecheux ................... A61F 5/04 606/59 |
| 5,643,089 | A | * | 7/1997 | Hummel ................. B25B 23/14 464/37 |
| 6,921,623 | B2 | | 7/2005 | Hanabata et al. |

(Continued)

FOREIGN PATENT DOCUMENTS

| | | |
|---|---|---|
| CN | 106859761 | 6/2017 |

OTHER PUBLICATIONS

Foreign Search Report on PCT/US2023/029632 Dtd Nov. 22, 2023.  
International Preliminary Report on Patentability on PCT/US2023/029632 dated Mar. 1, 2025.

*Primary Examiner* — Tarla R Patel  
(74) *Attorney, Agent, or Firm* — Foley & Lardner LLP

(57) ABSTRACT

The present disclosure is directed to a medical device. The medical device can include a first end having a first aperture, a first biasing member, a second aperture, and a second biasing member. Each of the first aperture and the second aperture can receive a portion of a bone component. The medical device can include a second end having a tensioning member that can apply force to at least a portion of the bone component.

20 Claims, 12 Drawing Sheets

(56)                References Cited

U.S. PATENT DOCUMENTS

| | | |
|---|---|---|
| 8,231,623 B1 | 7/2012 | Jordan |
| 10,973,673 B1 | 4/2021 | Skraber |
| 2004/0034350 A1 | 2/2004 | St. Onge et al. |
| 2015/0351779 A1* | 12/2015 | Slagle .................. A61G 13/101 |
| | | 211/85.13 |
| 2016/0022315 A1 | 1/2016 | Soffiatti et al. |
| 2018/0104801 A1* | 4/2018 | Bakula ................ B25B 23/1427 |
| 2022/0047312 A1* | 2/2022 | Seykora ............. A61B 17/1728 |

* cited by examiner

1105 — Provide device

1110 — Actuate locking cam

1115 — Receive portion of component

1120 — Apply force to component

1200

1205 — | Provide device |

FIG. 12

MEDICAL DEVICE

BACKGROUND

Various medical devices can be used to support several bones, muscles, ligaments, or tendons in a body.

SUMMARY

At least one aspect is directed to a medical device. The medical device can include a first end having a first aperture, a first biasing member, a second aperture, and a second biasing member. Each of the first aperture and the second aperture can receive a portion of a bone component. The medical device can include a second end having a tensioning member that can apply force to at least a portion of the bone component.

At least one aspect is directed to a method. The method can include providing a medical device. The medical device can include a first end having a first aperture, a first biasing member, a second aperture, and a second biasing member and a second end having a tensioning member. The method can include actuating the first biasing member and the second biasing member. The method can include receiving, by the first aperture, a first portion of a bone component. The method can include receiving, by the second aperture, a second portion of the bone component. The method can include actuating the tensioning member to apply force to the first portion and the second portion of the bone component.

At least one aspect is directed to a method. The method can include providing a medical device. The medical device can include a first end having a first aperture, a first biasing member, a second aperture, and a second biasing member. Each of the first aperture and the second aperture can receive a portion of a bone component. The medical device can include a second end having a tensioning member that can apply force to at least a portion of the bone component.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings:

FIG. 1 is an example perspective view of a medical device, in accordance with implementations.

FIG. 12 is an example illustration of a method, in accordance with implementations

DETAILED DESCRIPTION

Following below are more detailed descriptions of various concepts related to, and implementations of, methods, apparatuses, and systems of medical devices. The various concepts introduced above and discussed in greater detail below may be implemented in any of numerous ways.

Traction bows, often referred to as k-bows, can include medical devices that can engage with various components to aid medical professions during various medical operations or procedures, including surgery. The present disclosure generally relates to systems and methods for providing a medical device that can facilitate supporting one or more bones, muscles, or ligaments. For example, the present disclosure generally relates to a medical device (e.g., a k-bow) that can engage with a bone component (e.g., a pin that protrudes through a portion of a bone or another component). The medical device can include a first end having at least two automatic biasing locking cams operably coupled with respective apertures (e.g., slots or other openings). The locking cams can include one or more biasing components that can be compressed by movement of a lever arm in a first direction. When the lever arm is released, the locking cams can be automatically bias to engage with the bone component within one or more apertures by the biasing components. The medical device can include a second end having a handle region. The handle region can include or can be a part of a tensioning member. For example, the tensioning member can be or can include a fastener that can apply tension to the bone component at the first end to fix the bone component relative to the medical device. Therefore, the medical device can receive the bone component and can fix the bone component relative to the medical device so that a user or machine can pull the handle region to pull the bone component which further applies tension to a patient's bones, tendons, muscles, or another portion of the body. The present disclosure includes several advantages over conventional techniques. For example, the present disclosure provides a medical device that can be disposable and can be easily and efficiently operated by one person.

Figure 1:
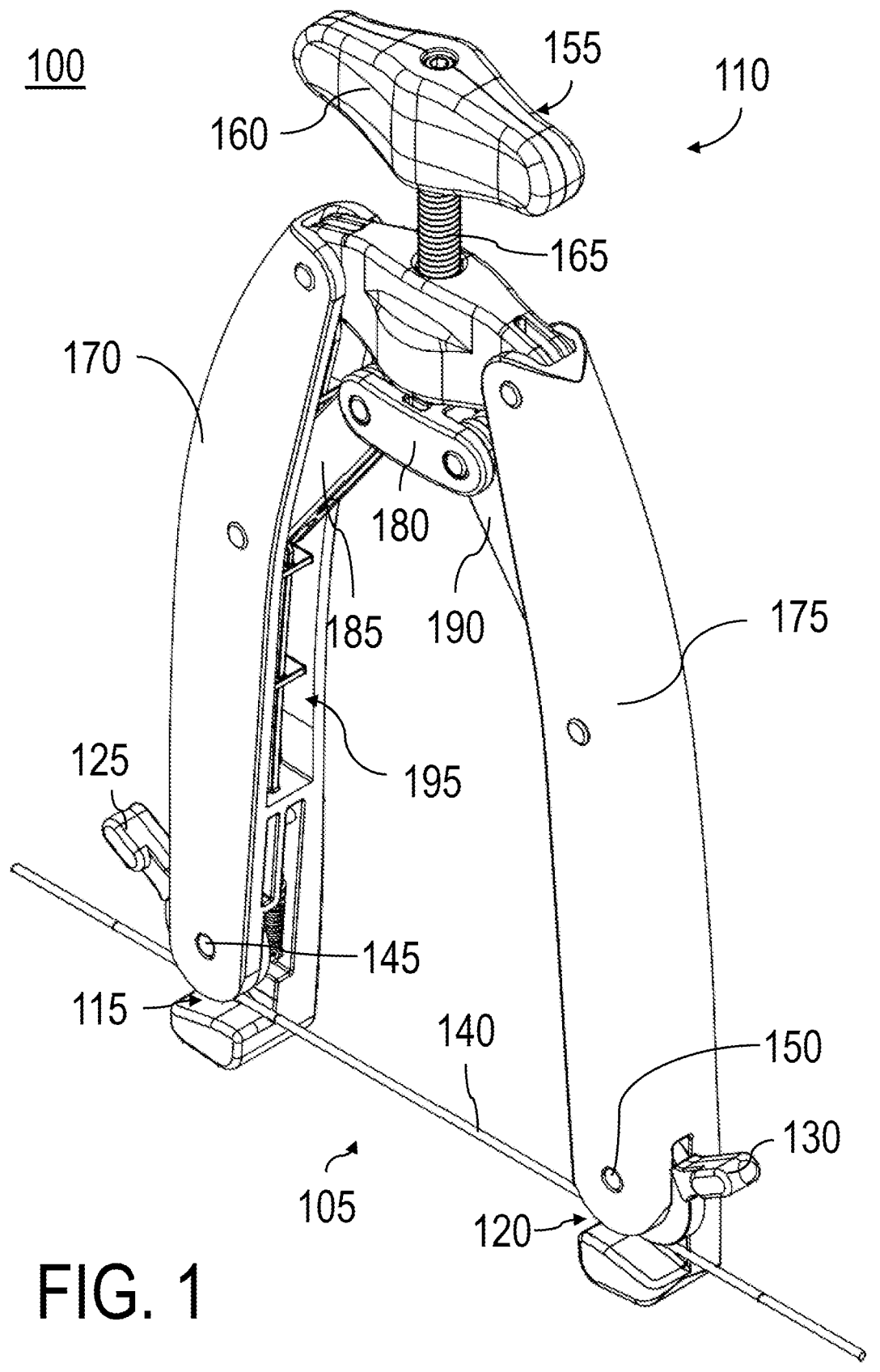
Figure 2:
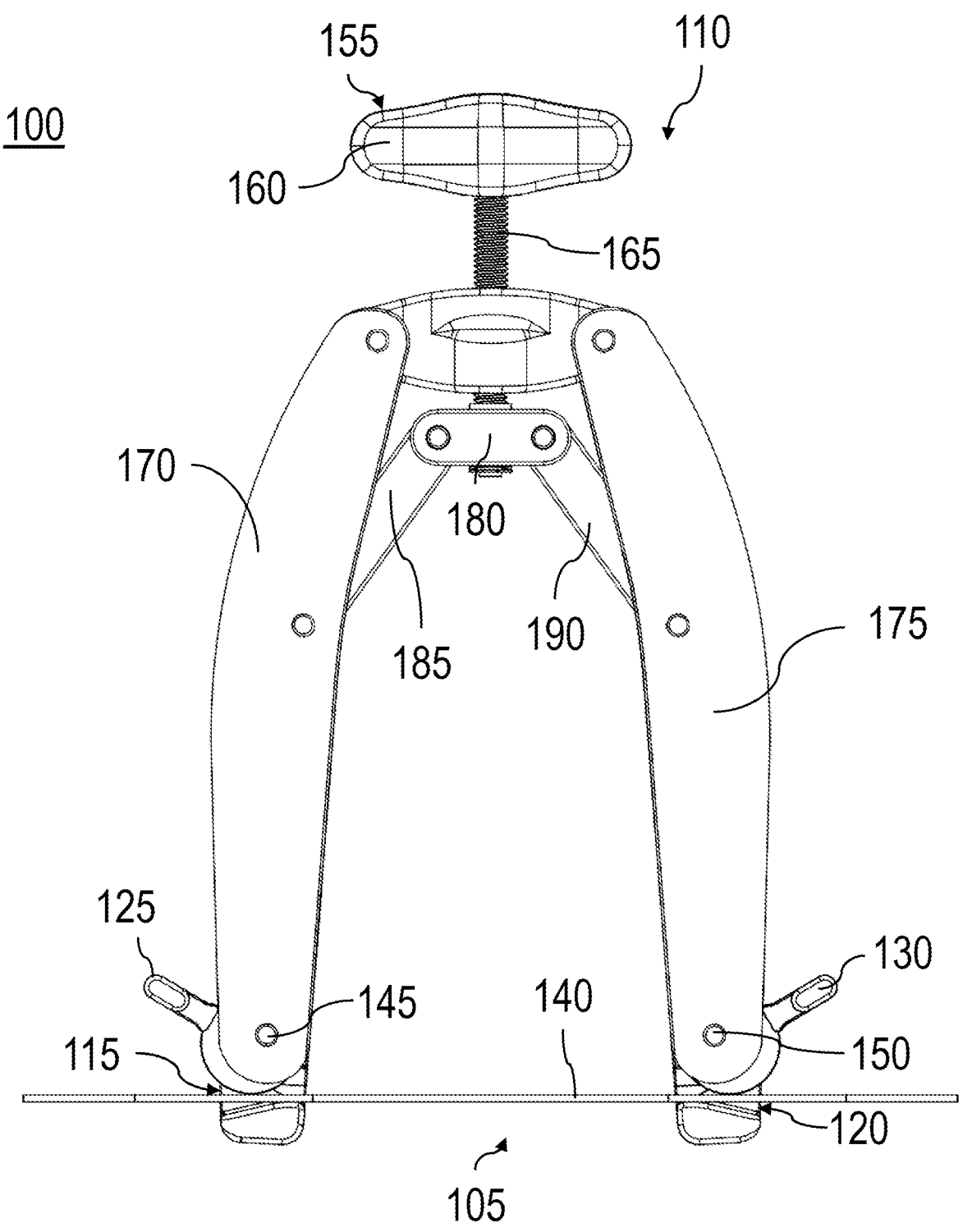
FIG. 2 is an example front view of the medical device of FIG. 1, in accordance with implementations.

FIG. 1 depicts an example perspective view of a device (e.g., a medical device) 100 and FIG. 2 depicts an example front view of the medical device 100, according to an example implementation. The medical device 100 can be used in one or more medical settings. For example, the medical device 100 can facilitate healing a patient, the medical device 100 can facilitate one or more medical professionals during operations or other activities, or the medical device 100 can be used in various other applications. For example, the medical device 100 can be used for a patient with a fractured hip, femur, or other bone. As described herein, the medical device 100 can be used to affix traction with a bone component (e.g., a pin, a wire, or another component).

The medical device 100 can include a first end 105 and a second end 110. The first end 105 can oppose the second end 110. The first end 105 can be positioned in other various positions relative to the second end 110 (e.g., adjacent to). The medical device 100 can include a first arm 170 that extends between the first end 105 and the second end 110. The medical device 100 can include a second arm 175 that extends between the first end 105 and the second end 110. The first arm 170 can oppose the second arm 175. The first arm 170 can adjustably couple with the second arm 175 by one or more adjusting members. For example, the first arm 170 and the second arm 175 can adjustably couple with one another by a linkage mechanism (e.g., a first linkage 180, a second linkage 185, and a third linkage 190). Movement of the linkage mechanism can cause the first arm 170 and the second arm 175 to move away from one another or towards one another, as described herein.

The first end 105 can include at least one locking cam. For example, the first end 105 can include two spring-loaded locking cams (e.g., first cam 125 and second cam 130). The spring-loaded locking cams can be or can include one or more nuts, screws, clamps (e.g., toggle clamps), cam mechanisms (e.g., wedge cams), ratchets, clamping levers, sliding mechanisms, or other components that can facilitate locking a device, apparatus, or component with the medical device 100 as described herein. The first end 105 can include at least one aperture that at least one cam engages with. For example, the first end 105 can include a first aperture 115 and a second aperture 120. The first aperture 115 and the second aperture 120 can be or can include one or more slots, grooves, holes, or other openings that can at least partially receive a bone component 140. The bone component 140 can be or can include a device, apparatus, component, or fixture that couples with or engages with one or more of a muscle, bone, tendon, or ligament of a patient. For example, the bone component 140 can be a pin or wire that can penetrate through a portion of a femur bone (e.g., a 2 mm stainless steel pin).

The first locking cam 125 can bias towards the first aperture 115 and the second locking cam 130 can bias towards the second aperture 120. For example, the first locking cam 125 can include one or more biasing components (e.g., one or more types of springs) that can bias the first locking cam 125 in a direction that substantially closes the first aperture 115 (e.g., a portion of the locking cam 125 at least partially blocks the aperture to close 50% or more of the aperture or a portion of the locking cam 125 at least partially contacts a portion of the bone component 140 received in the aperture). The second locking cam 130 can include one or more biasing components (e.g., one or more types of springs) that can bias the second locking cam 130 in a direction that substantially closes the second aperture 120 (e.g., a portion of the locking cam 130 at least partially blocks the aperture to close 50% or more of the aperture or a portion of the locking cam 130 at least partially contacts a portion of the bone component 140 received in the aperture).

The first locking cam 125 and the second locking cam 130 can be or can include at least one lever arm that can cause the biasing members to compress or release with movement of the lever arm. For example, the first locking cam 125 can include a rotatable portion rotatably coupled with the first arm 170 of the medical device 100 at a first pivot point 145 (e.g., one or more rivets, pins, or other components that rotatably couples the rotatable portion with the first arm 170). The rotatable portion can include a generally round or tear drop shape. The first pivot point 145 can be offset from the center point of the rotatable portion to apply the maximum force to the first aperture 115. For example, the first pivot point 145 can be between 1 mm and 10 mm (e.g., 5 mm) offset from a center portion of the first locking cam 125. The second locking cam 130 can include a rotatable portion rotatably coupled with the second arm 175 of the medical device 100 at a second pivot point 150 (e.g., one or more rivets, pins, or other components that rotatably couples the rotatable portion with the second arm 175). The rotatable portion can include a generally round or tear drop shape. The second pivot point 150 can be offset from the center point of the rotatable portion to apply the maximum force to the second aperture 120. For example, the second pivot point 150 can be between 1 mm and 10 mm (e.g., 5 mm) offset from a center portion of the second locking cam 130. The first locking cam 125 can include a lever arm portion that causes the rotatable portion to rotate about the first pivot point 145 responsive to a force applied on the lever arm portion. The second locking cam 130 can include a lever arm portion that causes the rotatable portion to rotate about the second pivot point 150 responsive to a force applied on the lever arm portion.

Figure 3:
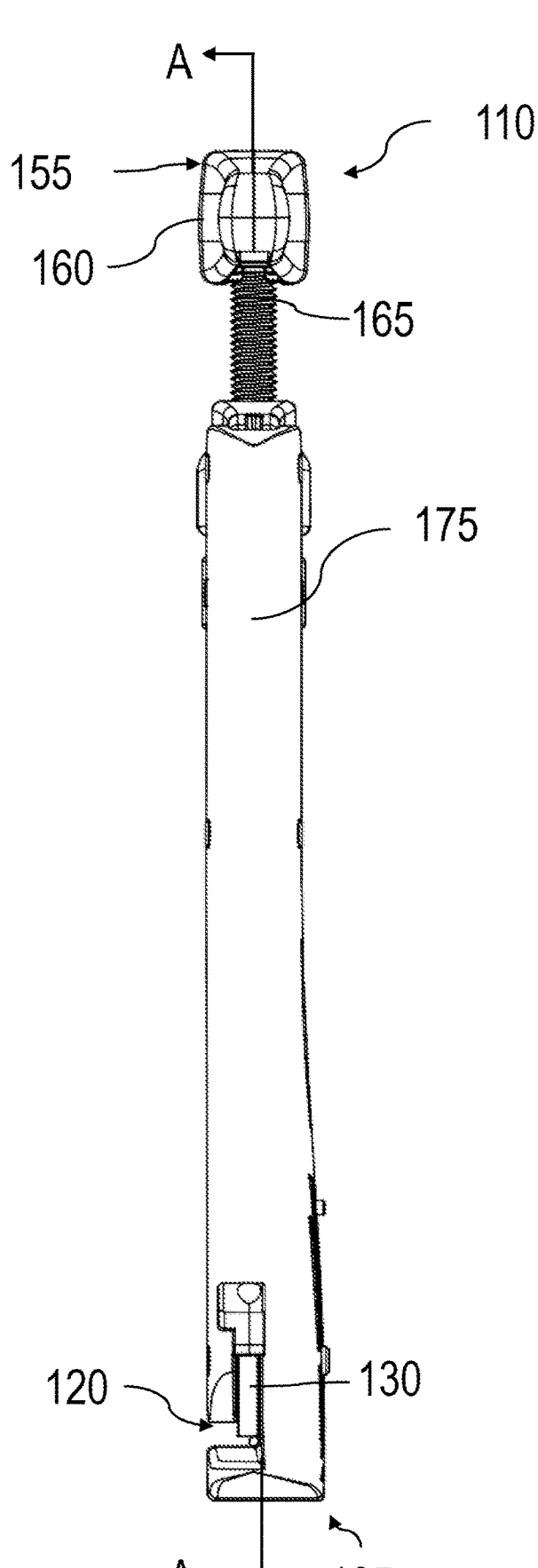
FIG. 3 is an example side view of the medical device of FIG. 1, in accordance with implementations.
Figure 4:
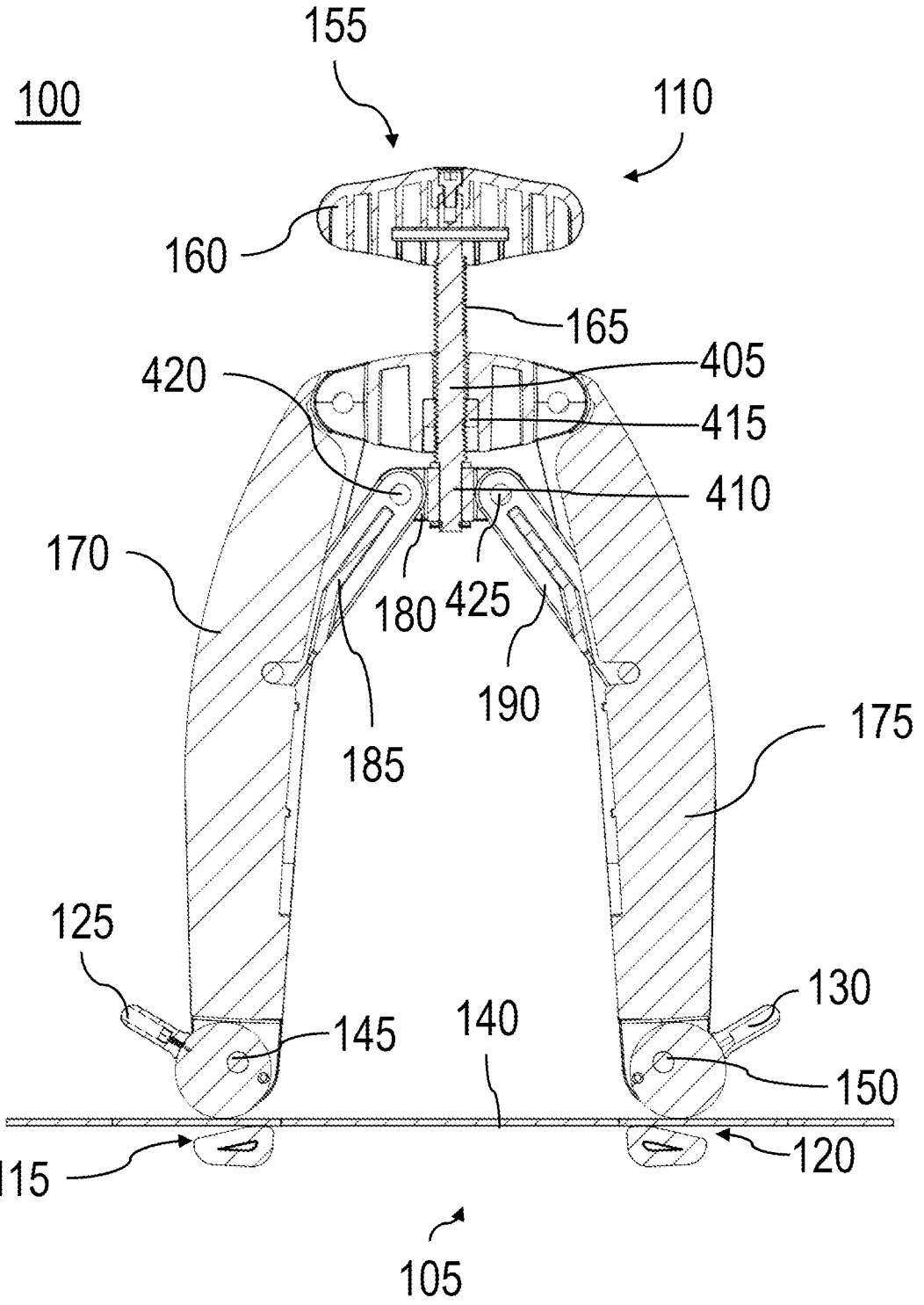
FIG. 4 is an example sectional view of the medical device of FIG. 1 cut along line A-A in FIG. 2, in accordance with implementations.

FIG. 3 depicts a side view of the medical device 100 and FIG. 4 depicts a sectional view of the medical device 100 cut along line A-A shown in FIG. 3. The second end 110 of the medical device 100 can include at least one tensioning member 155. The tensioning member 155 can apply force to at least a portion of the bone component 140. For example, the tensioning member 155 can include a fastener 165 that can operably couple with at least a portion of the linkage mechanism of the medical device 100. For example, as depicted in at least FIG. 4, the fastener 165 can include at least one threaded portion 405 and at least one fixed portion 410. The threaded portion 405 can threadably engage with a fixed threaded nut 415 of the medical device 100 such that the fastener 165 can move in at least one direction (e.g., up or down) by turning the fastener 165 relative to the fixed threaded nut 415. The fixed portion 410 can rigidly couple with a portion of the linkage mechanism (e.g., with the first linkage 180) such that the fastener 165 causes the first linkage 180 to move as the fastener 165 moves (e.g., up or down). Movement of the first linkage 180 can cause the second linkage 185 to rotate at the third pivot point 420 (e.g., one or more rivets, pins, or other components rotatably coupled with a first side of the first linkage 180) and the third linkage 190 to rotate at the fourth pivot point 425 (e.g., one or more rivets, pins, or other components rotatably coupled with a second side of the first linkage 180).

For example, turning the fastener 165 in a first direction can cause the fastener 165 to move in a downward direction (e.g., towards the first end 105). The movement of the fastener 165 can cause the first linkage 180 to simultaneously move in a direction towards the first end 105. The movement of the first linkage 180 can cause the second linkage 185 and the third linkage 190 to each rotate in a direction away from the first linkage 180. The second linkage 185 can couple with the first arm 170 (e.g., by one or more pins, riots, or other components) such that movement of the second linkage 185 (e.g., in a direction away from the first linkage 180) causes the first arm 170 to move (e.g., in a direction away from the first linkage 180). The third linkage 190 can couple with the second arm 175 (e.g., by one or more pins, riots, or other components) such that movement of the third linkage 190 (e.g., in a direction away from the first linkage 180) causes the second arm 175 to move (e.g., in a direction away from the third linkage 190). Therefore, downward movement of at least a portion of the tensioning member 155 causes the first arm 170 and the second arm 175 to move away from each other. When the bone component 140 is positioned within the first aperture 115 and the second aperture 120, movement of the first arm 170 and the second arm 175 in opposing directions can apply tension to the bone component 140 (e.g., by the first arm 170 and the second arm 175 pushing or pulling the bone component 140 by the first aperture 115 and the second aperture 120). The force applied to the bone component 140 by the first arm 170 and the second arm 175 by movement of the tensioning member 155 can fix the bone component 140 relative to the medical device 100.

Figure 8:
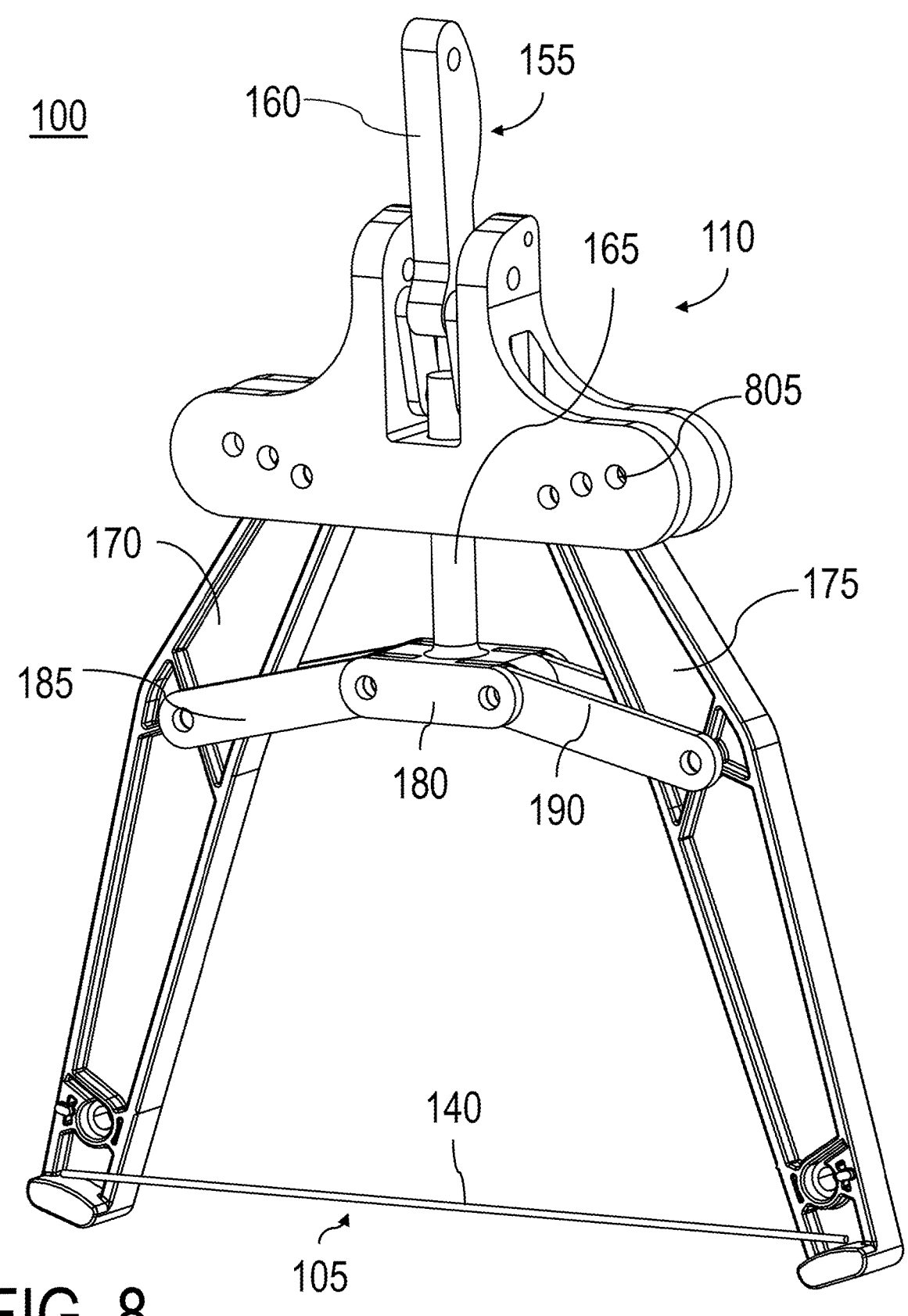
FIG. 8 is an example perspective view of a portion of the medical device of FIG. 1 in a first position, in accordance with implementations.
Figure 9:
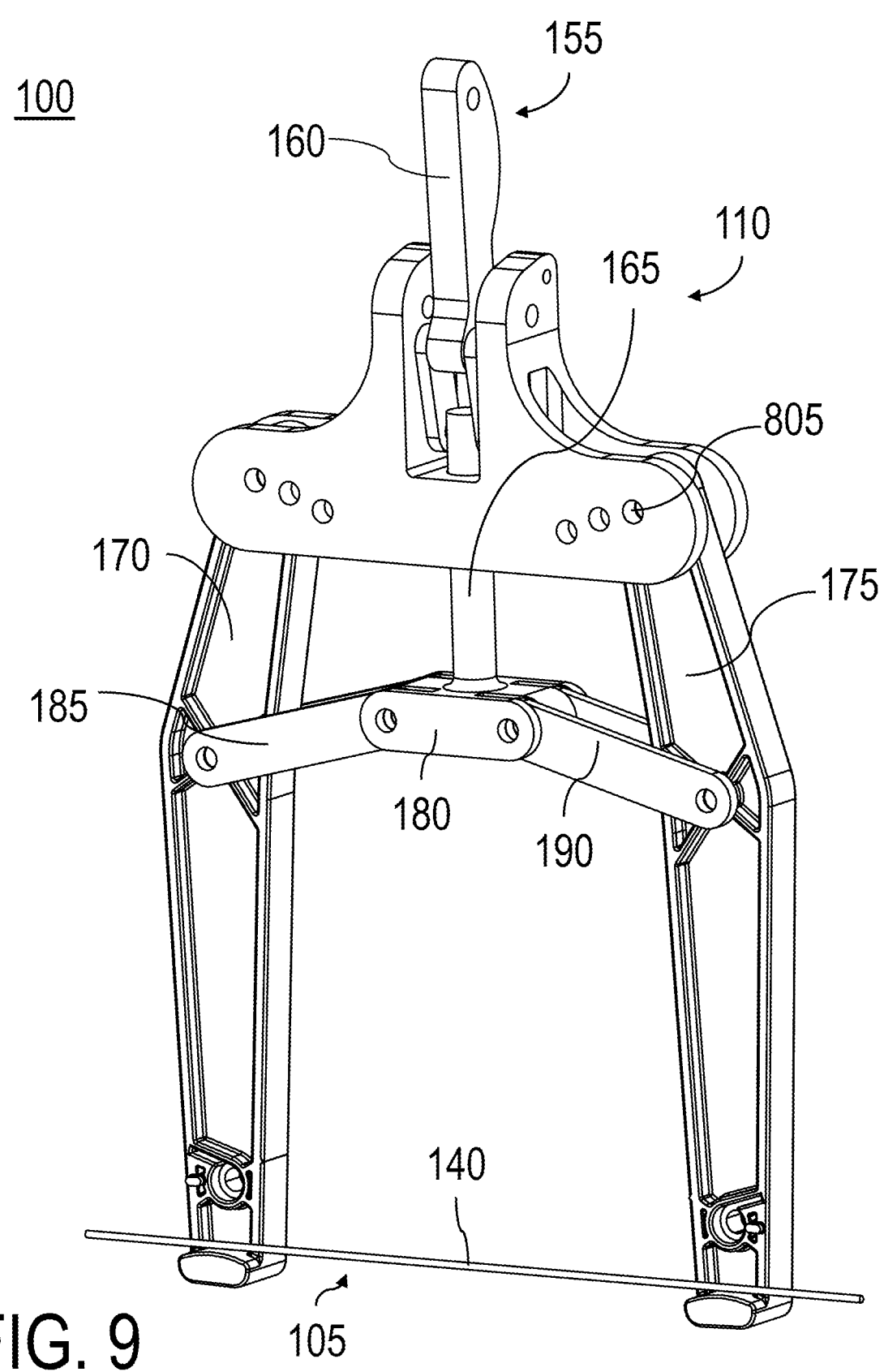
FIG. 9 is an example perspective view of a portion of the medical device of FIG. 1 in a second position, in accordance with implementations.

The medical device 100 can include one or more components that facilitate pre-setting a distance between the first arm 170 and the second arm 175 (e.g., a distance at the first end 105 of the medical device 100) prior to applying tension to the bone component 140. For example, the medical device 100 can include one or more pre-set locking components. For example, the medical device 100 can include one or more fastening components (e.g., pins, worm screws, springs, pins, or other components) that can facilitate positioning the first arm 170 and the second arm 175 in at least one position relative to one another (e.g., such that the first arm 170 and the second arm 175 may not freely move relative to one another). For example, as depicted in at least FIGS. 8 and 9, the pre-set distance between the first arm 170 and the second arm 175 can be adjusted via incremental holes 805 or slots in a top element at a hinge point of the arms or via incremental holes 805 or slots in the linkages of the medical device 100.

The locking cams can each be biased in the same direction. For example, the first locking cam 125 can bias towards the first aperture 115 such that a force applied to the first lever arm portion of the first locking cam 125 can cause a biasing member within the first locking cam 125 to compress. A force applied to the first lever arm portion of the first locking cam 125 can cause the first locking cam 125 to at least partially move away from the first aperture 115 to at least partially open the first aperture 115 (e.g., open 50% or more, open enough to receive a portion of the bone component 140). The second locking cam 130 can bias towards the second aperture 120 such that a force applied to the first lever arm portion of the second locking cam 130 can cause a biasing member within the second locking cam 130 to compress. A force applied to the first lever arm portion of the second locking cam 130 can cause the second locking cam 130 to at least partially move away from the second aperture 120 to at least partially open the second aperture 120 (e.g., open 50% or more, open enough to receive a portion of the bone component 140).

The tensioning member 155 can include at least one handle 160. The handle 160 can rigidly couple with the fastener 165 such that turning the handle 160 in one direction causes the fastener 165 to turn in the direction. The handle 160 can be sized or shaped for a hand or a user. For example, the handle 160 can include at least one curved section to interface with a portion of a hand. The handle 160 can include various positioning components. For example, the handle 160 can include at least one position selection component that facilitates moving or rotating the handle 160 in one or more alternative or additional positions. For example, the handle 160, or another portion of the tensioning member 155, can include at least one hinges or other components that can facilitate changing a position of the handle 160 responsive to one or more forces on the handle 160 (e.g., to move the handle 160 90 degrees, 180 degrees, or in another manner).

Figure 5:
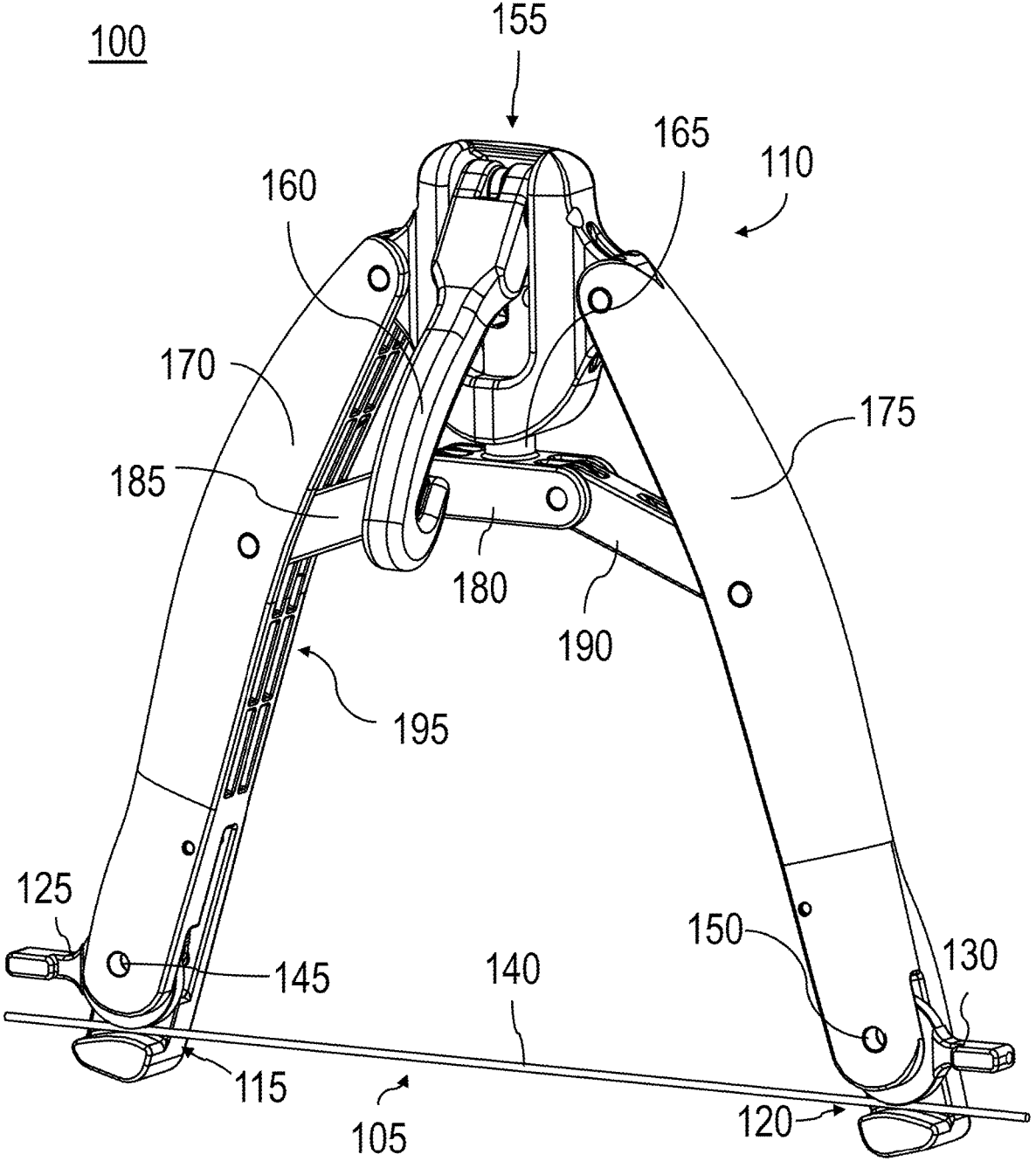
FIG. 5 is an example perspective view of the medical device of FIG. 1 in a first position, in accordance with implementations.
Figure 6:
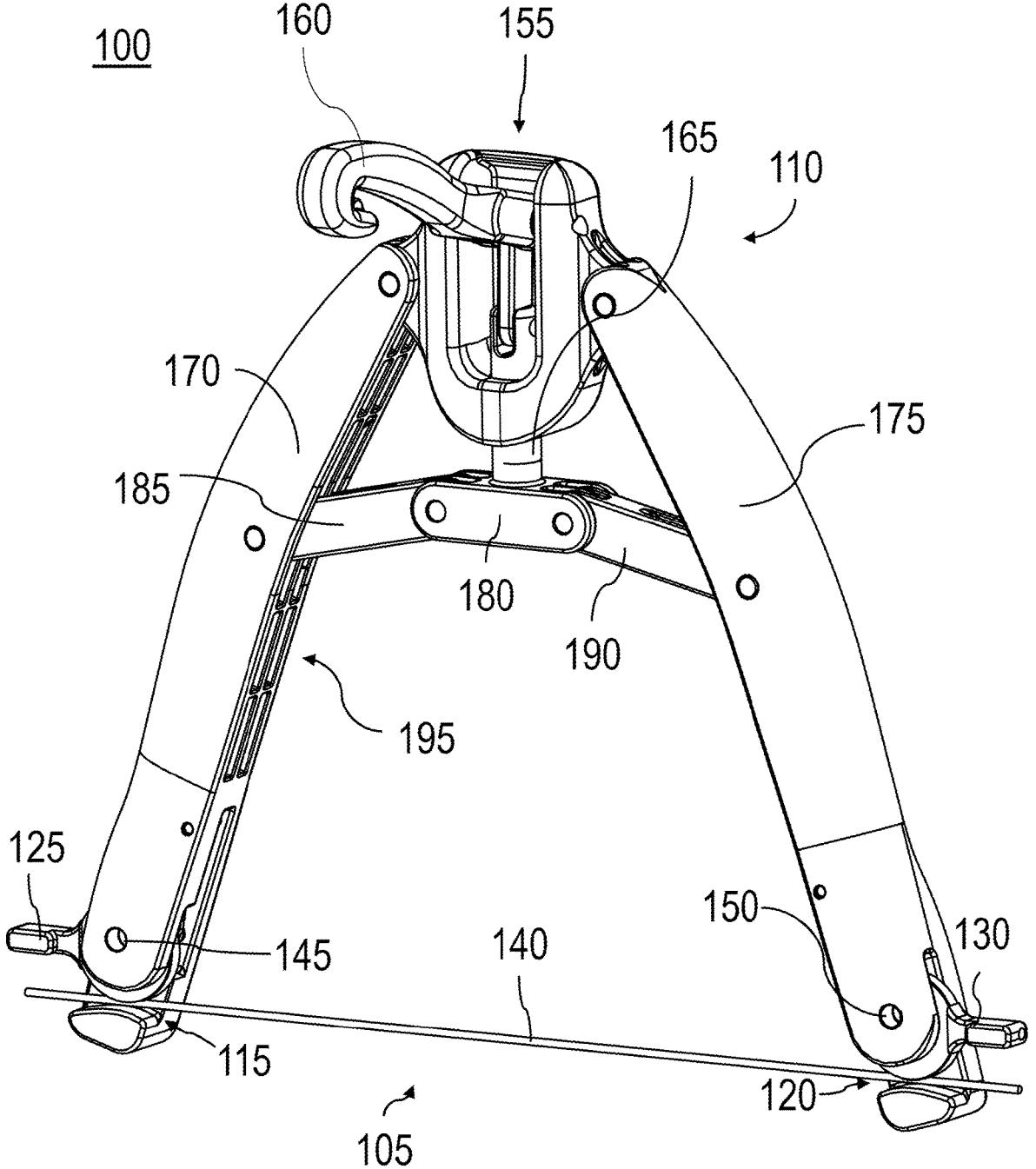
FIG. 6 is an example perspective view of the medical device of FIG. 1 in a second position, in accordance with implementations.
Figure 7:
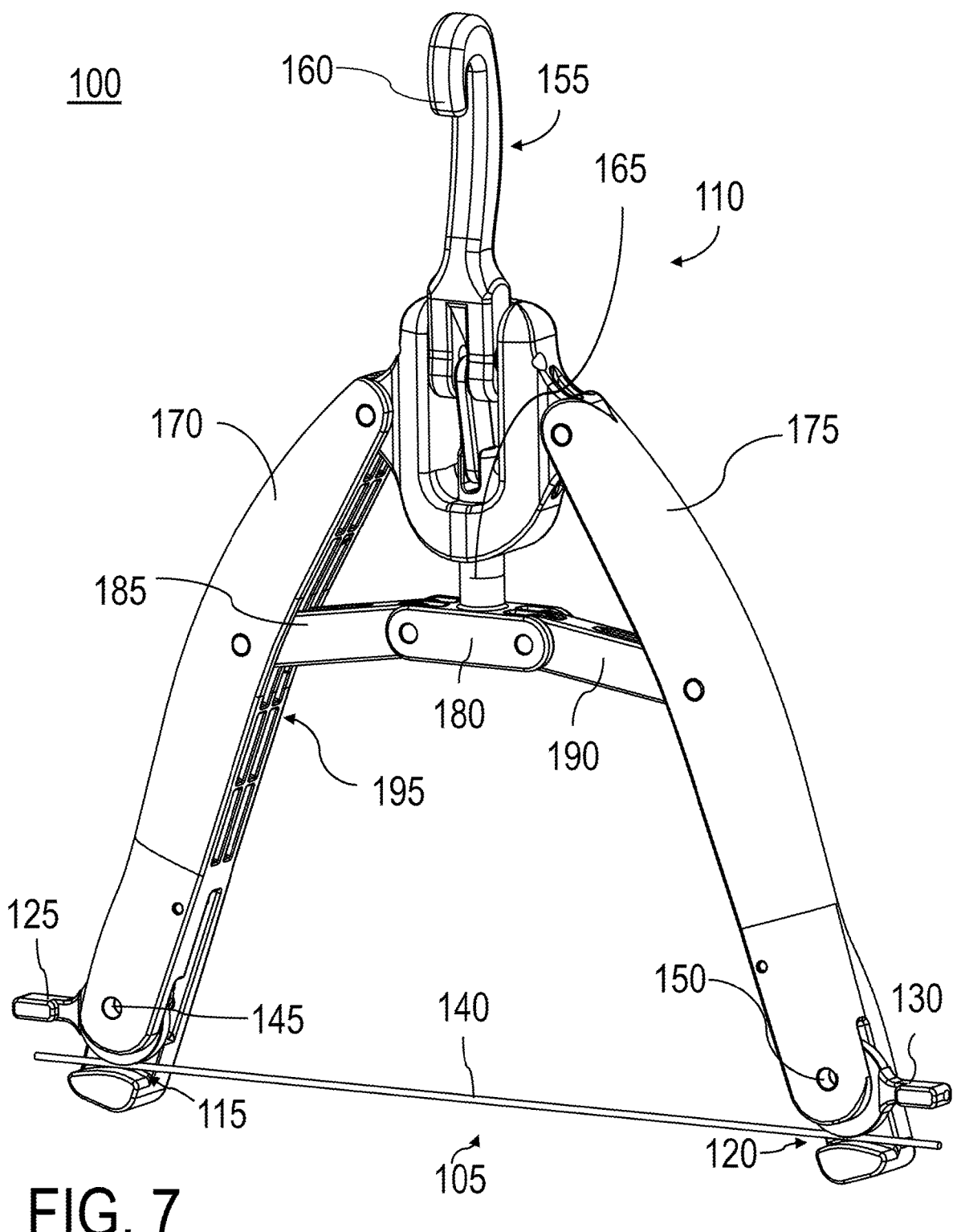
FIG. 7 is an example perspective view of the medical device of FIG. 1 in a third position, in accordance with implementations.

FIGS. 5-7 depict examples of the tensioning member 155. A depicted in FIGS. 5-7, and among others, the handle 160 can be or can include one or more lever arms, toggle switches, knobs, T-shaped handles, or various other components. The fastener 165 can be or can include one or more threaded components (e.g., screw, bolt, or another component) or the fastener 165 can include one or more non-threaded components. For example, the fastener 165 can include one or more rods that can push or pull a portion of the linkage mechanism (e.g., the first linkage 180) as depicted in at least FIG. 7. The handle 160 can include one or more toggle mechanisms (e.g., a toggle arm) as depicted in at least FIGS. 5-7. For example, FIG. 5 depicts the toggle handle 160 at a first state in which first arm 170 and the second arm 175 are a first distance apart from one another. FIG. 6 depicts the toggle handle 160 at a second state in which the handle 160 has been pulled such that the handle 160 causes the fastener 165 (e.g., rod) to push the first linkage 180 downward to begin separating the distance between the first arm 170 and the second arm 175. FIG. 7 depicts the toggle handle 160 at a third state in which the handle 160 has been pulled further such that the handle 160 causes the fastener 165 to push the first linkage 180 further downward to keep separating the distance between the first arm 170 and the second arm 175.

In operation, a user can grip one or more portions of the first arm 170 or the second arm 175 of the medical device 100. The user can apply force to both the lever arms of the first locking cam 125 and the second locking cam 130 simultaneously, or in series (e.g., using a thumb, a finger, or another component). The medical device 100 can include one or more textures, colors, or other features to facilitate identifying areas for a user to interact with. For example, the handle 160 or one or more portions of the first arm 170 or second arm 175 in which a user can grab or interact with can include one or more identifiable colors (e.g., blue, red, yellow, green, or another color) or detectable textures (e.g., ribs, grooves, bumps, brail, or other textures) that facilitate guiding a user. The portions of the medical device 100 in which a user may grab or interact with can differ from other portions of the medical device 100. For example, a portion of the handle 160 can be a different color or texture than a portion of the first linkage 180. With the lever arms engaged, the first locking cam 125 allows the first aperture 115 to receive a first portion of the bone component 140 and the second locking cam 130 allows the second aperture 120 to receive a second portion of the bone component 140. When the lever arms of the first locking cam 125 and the second locking cam 130 are released, the biasing component of the first locking cam 125 can bias a portion of the first locking cam 125 towards the first aperture 115 to engage (e.g., contact) the first portion of the bone component 140 and the biasing component of the second locking cam 130 can bias a portion of the second locking cam 130 towards the second aperture 120 to engage (e.g., contact) the second portion of the bone component 140. The biasing members of the first locking cam 125 and the second locking cam 130 can include enough strength (e.g., stiffness of spring) to fix the bone component 140 within the first aperture 115 and the second aperture 120 such that the bone component 140 may not fall from the first aperture 115 or the second aperture 120 by gravity only (e.g., without additional force applied to the bone component 140). For example, at least one spring of the first locking cam 125 or second locking cam 130 can include a length of about 15 mm-30 mm, an outer diameter of about 1 mm-10 mm, a maximum extended length of about 30 mm-45 mm, and a spring rate of about 0.1 kg/mm-0.25 kg/mm. At least one spring can be made of a stainless steel material.

With at least a portion of the bone component 140 received within the first aperture 115 or the second aperture 120, a user can grip or turn the handle 160 to rotate the fastener 165 of the tensioning member 155 (e.g., in one of a clockwise or counterclockwise direction). The rotation of the fastener 165 can cause the first linkage 180 to move in a downward direction towards the first end 105 of the medical device 100. The movement of the first linkage 180 can cause the second linkage 185 and the third linkage 190 to move in opposing directions. The movement of the second linkage 185 can cause the first arm 170 to move in an outward direction (e.g., away from the second arm 175). The movement of the third linkage 190 can cause the second arm 175 to move in an outward direction (e.g., away from the first arm 170). The movement of the first arm 170 and the second arm 175 in opposing directions can apply force (e.g., tension) to the portions of the bone component 140 received within the first aperture 115 and the second aperture 120. The force applied to the bone component 140 can strengthen the engagement between the locking cams 125, 130 and the bone component 140 such that the medical device 100 is rigidly fixed to the bone component 140 (e.g., the medical device 100 cannot move or rotate relative to the bone component 140). For example, the fastener 165 can make various numbers of full rotations (e.g., quarter rotation, half rotation, one rotation, two rotations, or more) to apply more tension force to the bone component 140.

A user can apply force to one or more portions of the tensioning member 155 (e.g., to the handle 160) to apply a force to the bone component 140. For example, a user can pull or push the handle 160 in one direction (e.g., in a direction towards the first end 105, in a direction away from the first end 105). For example, a user can use the handle 160 to pull or push one or more bones, tendons, or ligaments as the bone component 140 is rigidly coupled with the medical device 100. For example, the medical device 100 can be used to apply force to a portion of a fractured hip or femur (e.g., by the bone component 140 punctured or inserted through a portion of the hip or femur). A user can turn the handle 160 in an opposing direction to cause the first linkage 180 to move away from the first end 105 to lessen the force applied to the bone component 140. A user can engage the lever arms of the first locking cam 125 and the second locking cam 130 to release the bone component 140 from the first aperture 115 and the second aperture 120. Therefore, the medical device 100 can be easily operated by one user (e.g., by two hands).

Figure 10:
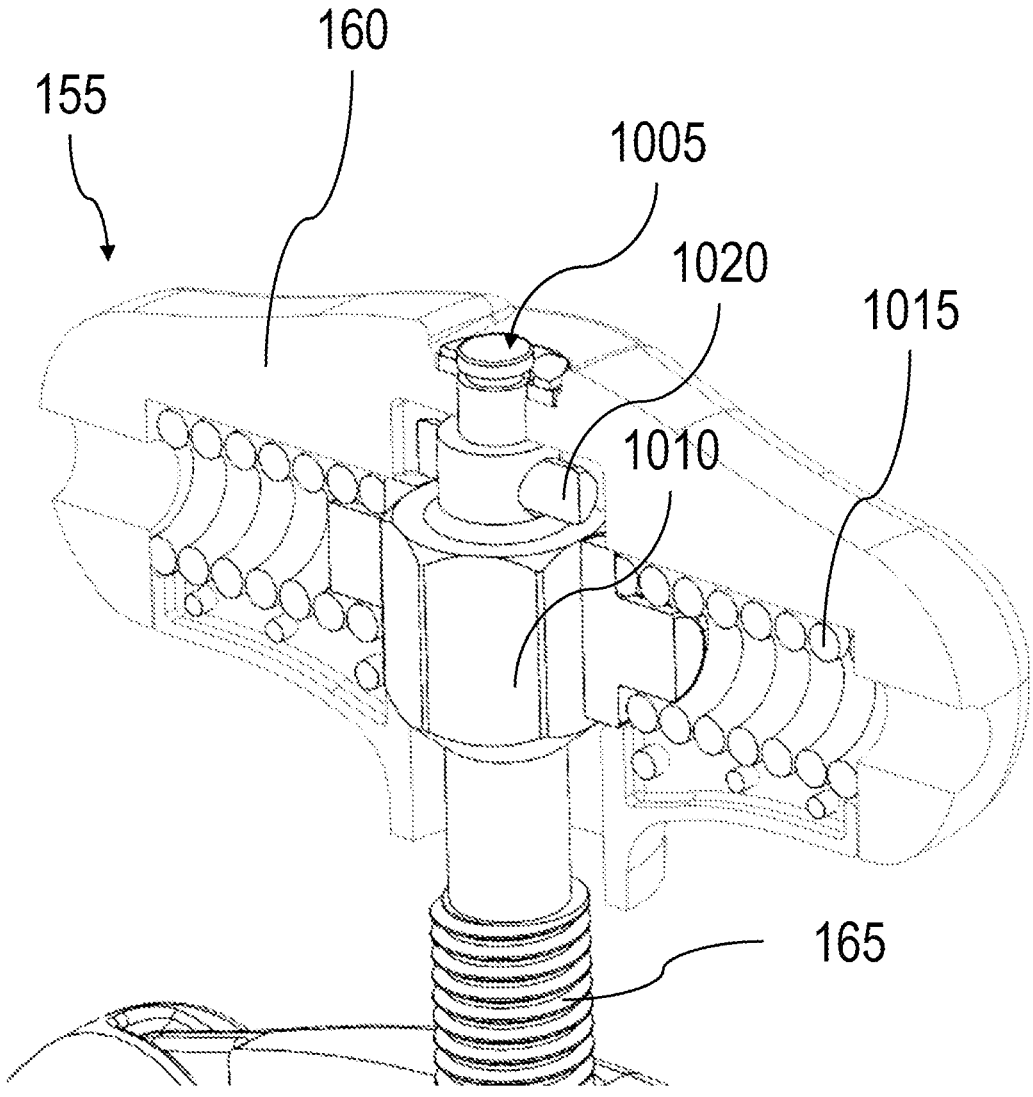
FIG. 10 is an example sectional view of a tensioning member of the medical device of FIG. 1, in accordance with implementations.

FIG. 10 depicts an example sectional view of a portion of the tensioning member 155. The tensioning member 155, or another portion of the medical device 100, can include at least one torque reduction mechanism 1005. For example, the tensioning member 155 can include one or more devices or systems that can facilitate preventing a maximum amount of torque applied to the tensioning member 155, the first linkage 180, or the bone component 140. For example, the tensioning member 155 can include one or more clutch mechanisms calibrated to a predetermined maximum torque. The clutch mechanism can include one or more clutches that disengage responsive to reaching the maximum torque to prevent applying more than the maximum torque to the fastener 165. The tensioning member 155 can include one or more torque indicators (e.g., digital or analog) that display a value of torque applied to the tensioning member 155. The medical device 100 can include one or more indicators (e.g., audio or visual) that notify a user if a maximum torque has been reached. The tensioning member 155 can include various additional or alternative torque limiters including, but not limited to, shear pins, magnetic torque limiters, or pneumatic torque limiters. Preventing the medical device 100 from reaching a maximum torque can facilitate reducing or preventing damage to the device 100 or to the bone component 140 in comparison with conventional techniques.

For example, at least a portion of the fastener 165 can include a hexagonal head 1010. The tensioning member 155 can include at least one spring 1015 positioned within the handle 160 that can provide rotational engagement against the flat surfaces of the hexagonal head 1010. When rotational torque is applied on the handle 160, the spring 1015 begins to compress and when a predetermined torque has been reached, the hexagonal head 1010, and in turn the fastener 165, can begin to rotate within the handle 160, which can limit how much more torque can be applied through the fastener 165. The torque reduction mechanism 1005 can include at least one dowel pin 1020 at a top of the faster 165 that can engage with the handle 160 to prevent the handle 160 from continuously slipping relative to the hexagonal head 1010 so that there is at least one initial slip when the predetermined torque is reached (e.g., to let the user know they have reached the predetermined torque), but the user can continue applying more torque when the dowel pin 1020 engages the handle 160. The torque reduction mechanism 1005 may not include the dowel pin 1020 such that the handle 160 keeps slipping when the predetermined torque has been reached.

The medical device 100 can include a variety of materials. For example, at least a portion of the medical device 100 (e.g., at least the first arm 170 or the second arm 175) can include one or more injection molded plastic materials. The medical device 100 can include a variety of non-metallic materials including, but not limited to, Nylon, Polyethylene Terephthalate (PET or PETE), High-Density Polyethylene (HDPE), Polyvinyl Chloride (PVC or Vinyl), Low-Density Polyethylene (LDPE), Polypropylene (PP), Polystyrene (PS or Styrofoam), elastomers, or other materials. The material of the handle 160 can be thicker in at least some portions than the material of another component of the medical device 100.

The medical device 100 can include one or more components that facilitate strengthening the medical device 100. For example, at least one of the first arm 170 or the second arm 175 can include one or more ribs 195. The ribs 195 can position along an inner portion of the first arm 170 or the second arm 175 (e.g., such that the ribs 195 face the other arm). For example, at least a portion of the first arm 170 or the second arm 175 can be hollow with one or more cross beams that form the ribs 195, as depicted in at least FIG. 1. The ribs 195 can extend in various directions. For example, the ribs 195 can extend between the first end 105 and the second end 110 of the medical device 100. The ribs 195 can extend perpendicular (e.g., from a first side of the first arm 170 to a second side of the first arm 170 or from a first side of the second arm 175 to a second side of the second arm 175). The ribs 195 can be formed on at least a portion of the first arm 170 or the second arm 175 or the ribs 195 can be formed on an entirety of the first arm 170 or the second arm 175. The ribs 195 can be formed on the inner portion of the first arm 170 or the second arm 175 such that the ribs 195 are not visible from the outer portions of the first arm 170 or the second arm 175 (e.g., opposing the inner portion). The ribs 195 can be formed from injection molded plastic or various other materials (e.g., other plastics or metallic materials).

The medical device 100 can include at least one type of metallic material. For example, at least a portion of the medical device 100 (e.g., the fastener 165) can include one or more of steel, aluminum, brass, copper, or another type of metallic material. The medical device 100 can be disposable. For example, a user can dispose of the medical device 100 after one or more uses. Disposing of the medical device 100 after use can facilitate reducing stripping of the threads of the fastener 165 over time.

Figure 11:
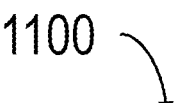
FIG. 11 is an example illustration of a method, in accordance with implementations.

FIG. 11 depicts a method 1100, according to an example implementation. The method 1100 can include providing the medical device 100, as depicted in act 1105. For example, the medical device 100 can be provided with one or more bone components 140. The medical device 100 can be provided pre-sterilized within a sterilized pouch or peel pack (e.g., a single use pouch or pack) to enhance sterilization and disposability of the medical device 100.

The medical device 100 can include the first end 105, the second end 110, a first arm 170 that extends between the first end 105 and the second end 110, and the second arm 175 that extends between the first end 105 and the second end 110. The first end 105 can include the first locking cam 125 that can open or close the first aperture 115 and the second locking cam 130 that can open or close the second aperture 120. The second end 110 can include the tensioning member 155. The tensioning member 155 can include the handle 160 or the fastener 165 that can rotate to expand the distance between the first arm 170 and the second arm 175 by one or more linkage mechanisms.

The method 1100 can include actuating at least one of the first locking cam 125 or the second locking cam 130, as depicted in act 1110. For example, the first lever arm of the first locking cam 125 can be actuated by applying a force in a direction to the first lever arm (e.g., in a direction towards the second end 110 of the medical device 100. The second lever arm of the second locking cam 130 can be actuated by applying a force in a direction to the second lever arm (e.g., in a direction towards the second end 110 of the medical device 100). For example, each lever arm can compress the biasing members of the locking cams 125, 130 to at least partially open the first aperture 115 and the second aperture 120. The locking cams 125, 130 can open the apertures simultaneously or in series.

The method 1100 can include receiving at least a portion of the bone component 140, as depicted in act 1115. For example, at least a portion of the first aperture 115 can receive at least a portion of the bone component 140. At least a portion of the second aperture 120 can receive at least a portion of the bone component 140. As described herein, the first aperture 115 and the second aperture 120 can include one or more slots, grooves, or other openings that can receive a portion of the bone component 140.

The method 1100 can include applying force to at least a portion of the bone component 140, as depicted in act 1120. For example, the tensioning member 155 can rotate in at least one direction (e.g., by the handle 160). The tensioning member 155 can cause at least the first linkage 180 to move in a direction towards the first end 105 of the medical device 100. The movement can cause the distance between the first arm 170 and the second arm 175 (e.g., by driving the arms in opposing directions) to increase at the first end 105 of the medical device 100 to apply tension to at least a portion of the bone component 140 received in the first aperture 115 and the second aperture 120.

The method 1100 can include applying force to the bone component 140 by pulling, pushing, or applying another force to the tensioning member 155 of the medical device 100 (e.g., by pulling the handle 160 in a direction away from the first end 105.

The method 1100 can include releasing the bone component 140 by first turning the tensioning member 155 in an opposing direction to release the tension force on the bone component 140. The lever arms of the locking cams 125, 130 can actuate to open the first aperture 115 and the second aperture 120 to release the bone component 140. The method 1100 can include discarding the medical device 100 after one use (e.g., use with one patient or use during one operation). For example, the entire medical device 100, or a portion of the medical device 100, can be discarded.

Figure 12:
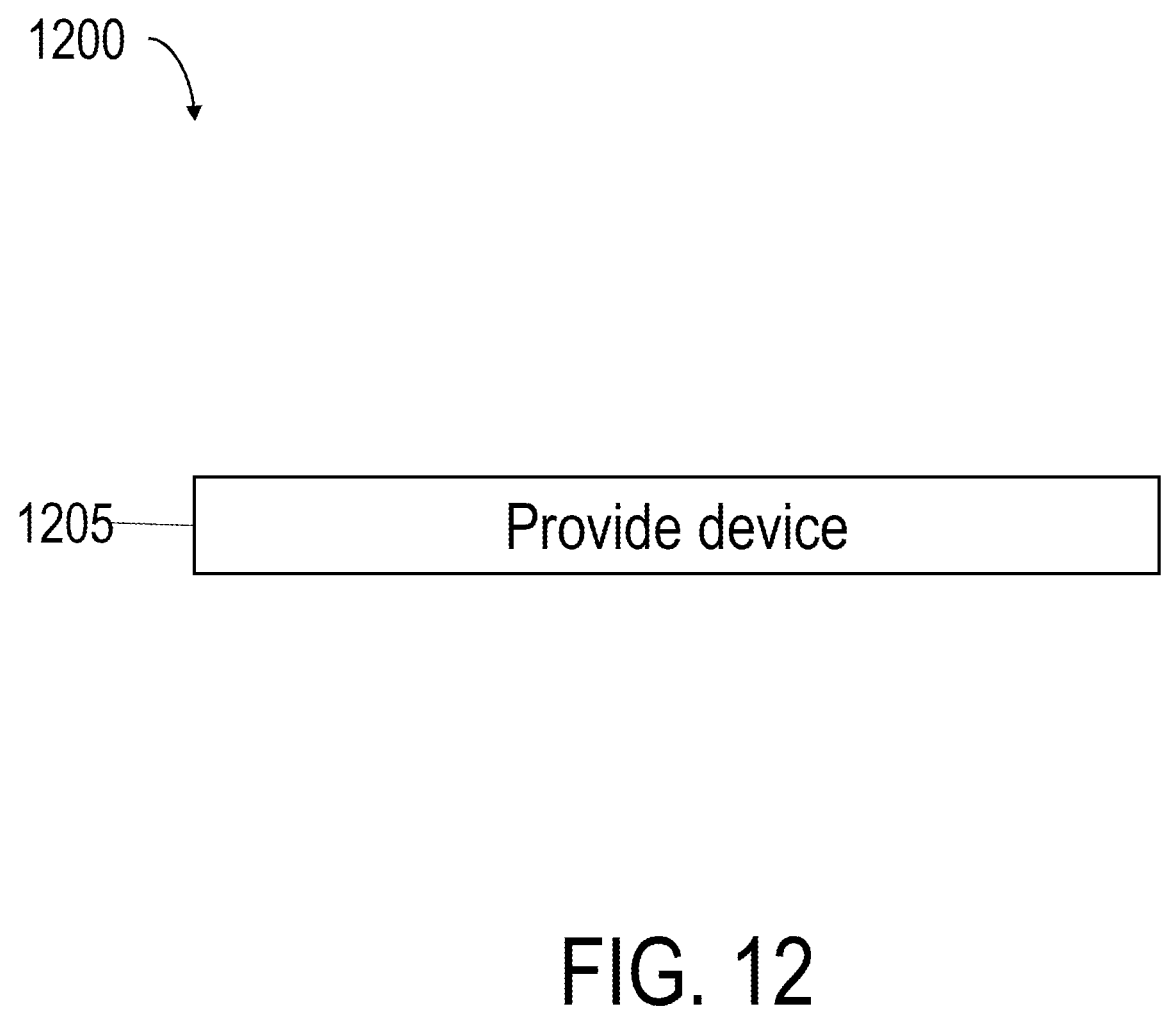

FIG. 12 depicts a method 1200, according to an example implementation. The method 1200 can include providing the medical device 100, as depicted in act 1205. The medical device 100 can include the first end 105, the second end 110, a first arm 170 that extends between the first end 105 and the second end 110, and the second arm 175 that extends between the first end 105 and the second end 110. The first end 105 can include the first locking cam 125 that can open or close the first aperture 115 and the second locking cam 130 that can open or close the second aperture 120. The second end 110 can include the tensioning member 155. The tensioning member 155 can include the handle 160 or the fastener 165 that can rotate to expand the distance between the first arm 170 and the second arm 175 by one or more linkage mechanisms.

The first lever arm of the first locking cam 125 can be actuated by applying a force in a direction to the first lever arm (e.g., in a direction towards the second end 110 of the medical device 100. The second lever arm of the second locking cam 130 can be actuated by applying a force in a direction to the second lever arm (e.g., in a direction towards the second end 110 of the medical device 100). For example, each lever arm can compress the biasing members of the locking cams 125, 130 to at least partially open the first aperture 115 and the second aperture 120. The locking cams 125, 130 can open the apertures simultaneously or in series.

At least a portion of the first aperture 115 can receive at least a portion of the bone component 140. At least a portion of the second aperture 120 can receive at least a portion of the bone component 140. The tensioning member 155 can rotate in at least one direction (e.g., by the handle 160). The tensioning member 155 can cause at least the first linkage 180 to move in a direction towards the first end 105 of the medical device 100. The movement can cause the distance between the first arm 170 and the second arm 175 (e.g., by driving the arms in opposing directions) to increase at the first end 105 of the medical device 100 to apply tension to at least a portion of the bone component 140 received in the first aperture 115 and the second aperture 120. The medical device 100 can be used, for example, to apply pressure to or separate a portion of a fractured femur or hip.

While operations are depicted in the drawings in a particular order, such operations are not required to be performed in the particular order shown or in sequential order, and all illustrated operations are not required to be performed. Actions described herein can be performed in a different order.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

Modifications of described elements and acts such as variations in sizes, dimensions, structures, shapes and proportions of the various elements, values of parameters, mounting arrangements, use of materials, colors, orientations can occur without materially departing from the teachings and advantages of the subject matter disclosed herein. For example, elements shown as integrally formed can be constructed of multiple parts or elements, the position of elements can be reversed or otherwise varied, and the nature or number of discrete elements or positions can be altered or varied. Other substitutions, modifications, changes and omissions can also be made in the design, operating conditions and arrangement of the disclosed elements and operations without departing from the scope of the present disclosure.

Systems and methods described herein may be embodied in other specific forms without departing from the characteristics thereof. For example, the medical device 100 can be used with various components including, but not limited to, a femoral component, a pelvic component, a tibia component, a skeletal component, a humeral component, a shoulder component, or other various components. Further relative parallel, perpendicular, vertical or other positioning or orientation descriptions include variations within +/−10% or +/−10 degrees of pure vertical, parallel or perpendicular positioning. References to "approximately," "about" "substantially" or other terms of degree include variations of +/−10% from the given measurement, unit, or range unless explicitly indicated otherwise. Coupled elements can be electrically, mechanically, or physically coupled with one another directly or with intervening elements. Scope of the systems and methods described herein is thus indicated by the appended claims, rather than the foregoing description, and changes that come within the meaning and range of equivalency of the claims are embraced therein.

What is claimed is:

1. A medical device, comprising:
a first end having a first aperture, a first biasing member, a second aperture, and a second biasing member;
each of the first aperture and the second aperture to receive a portion of a bone component;
the first biasing member including a spring-loaded locking cam having a lever arm portion and a body portion, the lever arm portion to cause the body portion to pivot between a first position, with the body portion enclosing the first aperture to fix the bone component within the first aperture, and a second position, with the body portion disposed apart from the first aperture to allow removal of the bone component from the first aperture;
a second end having a handle to apply force to the bone component; and
the handle including a torque reduction mechanism, the torque reduction mechanism including:
a fastener; and
a pin coupled to the fastener, the pin to engage with the handle.

2. The medical device of claim 1, comprising:
the fastener to engage with a linkage mechanism; and
the bone component comprises a second pin to be inserted through a portion of a bone.

3. The medical device of claim 1, comprising:
a first arm that extends between the first end and the second end;
a second arm that extends between the first end and the second end; and
the handle to apply the force to the bone component by driving the first arm and the second arm in opposing directions.

4. The medical device of claim 1, comprising:
the first biasing member biased towards the first position such that the body portion of the first biasing member is configured to at least partially contact the bone component in the first position.

5. The medical device of claim 1, comprising:

a first arm that extends between the first end and the second end;

a second arm that extends between the first end and the second end; and at least one of the first arm or the second arm includes a plurality of ribs.

6. The medical device of claim 1, comprising:

at least one disposable material; and at least one injection molded plastic material.

7. The medical device of claim 1, comprising:

at least one disposable material;

at least one injection molded plastic material; and at least one rib formed within the at least one injection molded plastic material.

8. The medical device of claim 1, comprising:

at least one of a portion of the handle or a portion of an arm that extends between the first end and the second end includes a textured material.

9. The medical device of claim 1, comprising:

the fastener including a hexagonal head defining a flat surface; and the torque reduction mechanism further including a spring to engage with the flat surface of the hexagonal head.

10. The medical device of claim 1, comprising:

a first arm that extends between the first end and the second end;

the first arm including a front surface, a rear surface, and a slot extending from the first aperture and between the front surface and the rear surface; and the body portion of the first biasing member at least partially disposed within the slot such that the body portion is integrated into the first arm.

11. The medical device of claim 1, comprising:

a first arm that extends between the first end and the second end;

the body portion of the first biasing member pivotably coupled with the first arm by a pivot point; and the pivot point offset from a center point of the body portion.

12. A method, comprising:

providing a medical device including a first end having a first aperture, a first biasing member, a second aperture, and a second biasing member and a second end having a handle, the first biasing member and the second biasing member each including a spring-loaded locking cam having a lever arm portion and a body portion, the lever arm portion to cause the body portion to pivot between a first position, with the body portion closing the first or second aperture to fix a bone component within the first or second aperture, and a second position, with the body portion disposed apart from the first or second aperture to allow removal of the bone component from the first or second aperture;

actuating the lever arm portions of the first biasing member and the second biasing member to pivot the body portions to the second position;

receiving, by the first aperture, a first portion of the bone component;

receiving, by the second aperture, a second portion of the bone component;

releasing the lever arm portions of the first biasing member and the second biasing member to pivot the body portions to the first position; and actuating the handle to apply force to the first portion and the second portion of the bone component;

the handle including a torque reduction mechanism, the torque reduction mechanism including:

a fastener; and a pin coupled to the fastener, the pin to engage with the handle.

13. The method of claim 12, comprising:

the fastener to engage with a linkage mechanism; and the bone component comprises a second pin to be inserted through a portion of a bone.

14. The method of claim 12, comprising:

a first arm that extends between the first end and the second end;

a second arm that extends between the first end and the second end; and actuating the handle includes driving the first arm and the second arm in opposing directions.

15. The method of claim 12, comprising:

the first biasing member biased towards the first position such that the body portion of the first biasing member is configured to at least partially contact the bone component in the first position.

16. The method of claim 12, comprising:

a first arm that extends between the first end and the second end;

a second arm that extends between the first end and the second end; and at least one of the first arm or the second arm includes a plurality of ribs.

17. The method of claim 12, comprising:

disposing the medical device.

18. The method of claim 12, comprising:

the fastener including a hexagonal head defining a flat surface; and the torque reduction mechanism further including a spring to engage with the flat surface of the hexagonal head.

19. A method, comprising:

providing a medical device, the medical device including:

a first end having a first aperture, a first biasing member, a second aperture, and a second biasing member;

each of the first aperture and the second aperture to receive a portion of a bone component;

the first biasing member including a spring-loaded locking cam having a lever arm portion and a body portion, the lever arm portion to cause the body portion to pivot between a first position, with the body portion closing the first aperture to fix the bone component within the first aperture, and a second position, with the body portion disposed apart from the first aperture to allow removal of the bone component from the first aperture;

a second end having a handle to apply force to the bone component; and the handle including a torque reduction mechanism, the torque reduction mechanism including:

a fastener; and a pin coupled to the fastener, the pin to engage with the handle.

20. The method of claim 19, comprising:

the fastener to engage with a linkage mechanism; and the bone component comprises a second pin to be inserted through a portion of a bone.

* * * * *